United States Patent [19]
Hammond et al.

[11] 3,995,058
[45] Nov. 30, 1976

[54] TREATMENT OF ETHANOL WITHDRAWAL SYMPTOMS WITH LEVODOPA

[75] Inventors: Michael Douglas Hammond, Chesham; Cyril Schneider, Whitton, both of England

[73] Assignee: Miles Laboratories, Inc., Elkhart, Ind.

[22] Filed: July 28, 1975

[21] Appl. No.: 599,449

Related U.S. Application Data

[63] Continuation of Ser. No. 424,348, Dec. 12, 1973, abandoned.

[52] U.S. Cl. ............................................. 424/319
[51] Int. Cl.² ...................................... A61K 31/195
[58] Field of Search ................................... 424/319

[56] References Cited
UNITED STATES PATENTS 3,646,213   2/1972   Bartholini .......................... 424/319

OTHER PUBLICATIONS

Salamon, Current Therapy, "Alcoholism", (1970), pp. 613–617.
Merck Manual 12th Edition, 1972, pp. 1417–1422.

*Primary Examiner*—Norman A. Drezin
*Attorney, Agent, or Firm*—Myron B. Sokolowski

[57] ABSTRACT

Levodopa or a composition comprising levodopa and a peripheral dopa decarboxylase inhibitor prevents or suppresses ethanol withdrawal symptoms in individuals abstaining from ethanol in a post-intoxicated state.

3 Claims, No Drawings

TREATMENT OF ETHANOL WITHDRAWAL SYMPTOMS WITH LEVODOPA

This is a continuation of application Ser. No. 424,348, filed Dec. 12, 1973, now abandoned.

BACKGROUND OF THE INVENTION

1. Field of the Invention

This invention relates to therapy of ethanol withdrawal symptoms in individuals deprived of or abstaining from ethanol after ethanol intoxication. For convenience, the terms *ethanol withdrawal symptoms* and *ethanol* are used interchangeably with *withdrawal symptoms* and *alcohol*, respectively, throughout the text of this specification.

Prevention or suppression of withdrawal symptoms currently is part of therapeutic regimens directed at the cure of a clinical entity known as alcoholism. Although the latter is a complex disease comprising psychological as well as physical aspects, it always involves a varying degree of physical dependence on alcohol caused by a chronic abuse thereof. A common therapeutic regimen involves abstinence from ethanol to reverse the physical dependence thereon and treatment of withdrawal symptoms precipitated by such abstinence with a variety of drugs. Pentobarbital, chloral hydrate, paraldehyde and chlordiazepoxide are generally used to prevent or suppress such symptoms (Granville-Grossman, *Recent Advances in Clinical Psychiatry*, J. & A. Churchill Co., Ltd., London, pp. 129–139 [1971]). Although phenothiazines, such as promazine and chlorpromazine, are indicated in cases in which the physical dependence is moderate, their use is limited in severe cases and is ineffective to prevent delirium tremors or seizures (Thomas and Freedman, J. Am. Med. Ass'n., 188: 316 [1964]; and, Golbert et al., J. Am. Med. Ass'n., 201: 99 [1967]).

2. Description of the Prior Art

Levodopa is the trivial nomenclature for the naturally occurring compound, L-$\beta$-3,4-dihydroxyphenylalanine. This compound is commercially available, and its synthesis has been reported in the literature (Yamada et al., Chem. Pharm. Bull., 10: 693 [1962]).

Known therapeutic uses of levodopa include treatment of the following disease entities: idiopathic and postencephalic parkinsonism, several extrapyramidal neuropathies, and depression.

The most widely recognized therapeutic use of levodopa is in the treatment of idiopathic and postencephalic parkinsonism (Cotzias et al., New Eng. J. Med., 276: 374 [1967]; and Yahr et al., Trans. Am. Neurol. Assn., 93: 56 [1968]). The mechanism of levodopa in the treatment of this disease is attributed to its presumed role in the correction of an imbalance of dopamine and acetylcholine in the basal ganglia, a biochemical defect associated with parkinsonism (Calne, Brit. Med. J., 2: 693 [1971]). The usual daily dosage of levodopa required to suppress the tremors of parkinsonism is from 4 to 5 g; a lower dose is effective if peripheral dopa decarboxylase inhibitors are administered in conjunction with levodopa. Examples of such peripheral dopa decarboxylase inhibitors which have been used with levodopa are: N'-(D,L-seryl)-N''-(2,3,4-trihydroxybenzyl)hydrazine (Barbeau et al., Clin. Pharmac. Ther., 12: 353 [1971]); and $\alpha$-methyl-dopa hydrazine (Cotzias et al., New Eng. J. Med., 280: 337 [1969]).

Levodopa also has been utilized to treat other extrapyramidal disorders such as those frequently observed after manganese poisoning (Mena et al., New Eng. J. Med., 282: 5 [1970]), supranuclear palsy (Klawans and Ringel, Europ. Neurol., 5: 115 [1971]), and hepatic coma (Parkes et al., Lancet 2: 1341 [1970]).

Therapeutic use of levodopa in the treatment of depression has been attempted but has proven to be of questionable value (Bunney et al., Lancet, 1: 885 [1969]; and Bunney et al., Lancet, 2: 352 [1970]).

In experiments attempting to implicate dopamine with sleep production in mice, a single dose of levodopa (400 mg/kg) produced a three-fold increase in sleeping time. However, this effect became smaller with increasing numbers of doses. Examination of brain catecholamines indicated an increasing shift of brain levels from dopamine to noradrenaline with increasing doses of levodopa. (Blum et al., Nature, 242: 407 [1973]).

SUMMARY OF THE INVENTION

The subject matter of this invention is a new therapeutic use of levodopa in the prevention or suppression of ethanol withdrawal symptoms in an individual abstaining from or deprived of ethanol after intoxication therewith. This invention also concerns compositions comprising levodopa and a peripheral decarboxylase inhibitor and use of such compositions in the prevention or suppression of ethanol withdrawal symptoms. The term *individual*, as utilized in the text of this specification and in the claims, refers either to a human being or to a mammal serving as a model for a human being in a laboratory experiment.

Abrupt discontinuation of and subsequent abstinence from ethanol in an individual after ethanol intoxication precipitate withdrawal symptoms, the intensity of which depends upon the degree and duration of the intoxication.

Mild symptoms of withdrawal occur after a single event of several or more hours of intoxication and may include headache, dizziness, weakness, perspiration, mild gastro-intestinal disturbances, and general malaise (Goldberg, Q. J. Stud. Alcohol. Suppl. 1: 37 [1961]).

Chronic intoxication with ethanol produces a state of physical dependence thereon, commonly referred to as alcoholism (Isbell et al., Q. J. Stud. Alcohol, 16: [1955]). In individuals physically dependent upon ethanol, withdrawal symptoms occur within a few hours of ethanol abstinence and commonly include tremor, nausea, moderate-to-severe gastro-intestinal disturbances, anxiety, insomnia, hallucinations, and even delirium and seizures. (Victor and Adams, Res. Publs. Assn. Res. Nerv. Ment. Dis., 32: 526 [1953]).

A suitable model of assessing the efficacy of drugs in the treatment of alcohol dependence in mice has been published in the literature (Hammond and Schneider, Brit. J. Pharmacol., 47: 667P [1973]). The characteristic withdrawal symptoms precipitated in ethanol-dependent mice upon deprivation of alcohol are similar to those observed in mice given drugs which produce hallucination in man (Corne and Pickering, Psychopharmacologia [Berl.], 11: 65 [1967]).

An unexpected new therapeutic use of levodopa in the prevention or suppression of withdrawal symptoms has been discovered utilizing the above model. Specifically, this invention involves the prevention or suppression of ethanol withdrawal symptoms in an individual abstaining from ethanol after intoxication therewith by administration to the individual of an effective amount of levodopa to prevent or suppress the withdrawal symptoms. The amount of levodopa required to effect such therapy ranges from 63 mg/kg to 1213 mg/kg, and the median effective dose ($ED_{50}$) required to prevent or suppress withdrawal symptoms is 231 mg/kg.

Withdrawal symptoms may also be prevented or suppressed in individuals by compositions from one to ten parts by weight of levodopa and one part by weight of a peripheral dopa decarboxylase inhibitor. Doses of the above-described compositions may range from 6 mg/kg to 33 mg/kg. The former limit represents a dose of 3 mg/kg of levodopa and 3 mg/kg of a peripheral dopa decarboxylase inhibitor (a ratio of 1:1) while the latter limit represents a dose of 30 mg/kg of levodopa and 3 mg/kg of the inhibitor (a ratio of 10:1). A preferred dose is 15 mg/kg, which comprises 12 mg/kg of levodopa and 3 mg/kg of the inhibitor (a ratio of 4:1). A preferred composition comprises 4 parts by weight of levodopa and 1 part by weight of said inhibitor. Examples of peripheral dopa decarboxylase inhibitors include N'-(D,L-seryl)-N''-(3,4,5-trihydroxybenzyl)-hydrazine, the hydrochloride or maleate salt thereof, and α-methyl-dopa hydrazine, all of which have been demonstrated to be useful in the control of parkinsonism tremor (Barbeau et al., Clin. Pharmacol. and Therap., 12: 353 [1971]). Peripheral dopa decarboxylase inhibitors may potentiate the action of levodopa in the treatment or prevention of ethanol withdrawal symptoms in individuals by enabling larger amounts of levodopa to reach the brain. Without intent to be limited to theory, it is believed that the action of levodopa in the prevention or suppression of ethanol withdrawal symptoms in individuals is a function of its antiserotonin effect. The neurotransmitter serotonin is postulated to be involved in the mediation of withdrawal symptoms in the experimental model described above. There is considerable evidence that catecholamines antagonize the action of serotonin in some parts of the central nervous system (Calcutt et al., *Agonist and Antagonist Actions of Narcotic Analgesic Drugs*, Kosterlitz et al., Eds., MacMillan, London, pp 176–191 [1972]). Furthermore, it has been found that noradrenaline given by intracerebral injection and amphetamine sulphate given subcutaneously produce a complete suppression of head-twitches in mice undergoing ethanol withdrawal. This observation together with the fact that α-methyl p-tyrosine, which inhibits catecholamine synthesis, also produces withdrawal symptoms that can be reduced by anti-serotonin agents, lead to the hypothesis that levodopa suppresses or prevents withdrawal symptoms because of its anti-serotonin effect.

Doses of levodopa or of the compositions may be administered orally or by other conventional routes of administration.

DESCRIPTION OF THE PREFERRED EMBODIMENTS

EXAMPLE 1

Male T/O mice were habituated to ethanol by oral administration of aqueous ethanol solutions over three days. Ethanol was administered as a 40% w/v solution, the animals receiving 4 g/kg on the first day, 5 g/kg on the second day and 6 g/kg on the third day. Twenty-four hours after the third dose, approximately 12 hours after blood ethanol had fallen to zero, mice were observed over a period of 4 minutes in groups of five and the number of head-twitches were recorded for each animal. All animals received two doses of levodopa or vehicle, one 6 hours after the last dose of ethanol and the other one hour before observation of the animals. The amount of discoordination produced by each treatment was also determined by measuring the animals' ability to remain for 1 minute on a drum, 30 cm diameter, rotating at a speed of 1 rpm. Using a quantal method the median effective dose ($ED_{50}$) to suppress head-twitches was determined. Since none of the animals were discoordinated, no value could be obtained for the median falling dose ($FD_{50}$). The ratio $FD_{50}$ to $ED_{50}$ gives the therapeutic ratio. Results are presented in the following table together with comparable values for ethanol, pentobarbitone sodium and also for compounds raising noradrenaline levels by release (amphetamine) and by its direct application to the brain.

TABLE

Potency of drugs in reducing ethanol withdrawal head-twitches and in causing discoordination in mice

| Drug | Route | ED 50 value to reduce head-twitches (with 95% fiducial limits) in mg/kg | FD 50 value for discoordination (with 95% fiducial limits) in mg/kg | FD 50 / ED 50 |
|---|---|---|---|---|
| Ethanol | P.O. | 3990 (2610–6410) | 2500 (2020–3140) | 0.6 |
| Pentobarbitone sodium | P.O. | 231 | 91 (36–229) | 0.4 |
| Amphetamine sulphate | S.C. | 7.18 | NT | NA |
| L-DOPA | P.O.* | 231.5 (63–1213) | >> 800** | 3.5 |
| Noradrenaline | I.C.V. | 0.003 | >>0.01** | >>>3.3 |

All drugs given one hour before observation except noradrenaline (35 minutes). Doses are expressed as mg/kg orally (P.O.), subcutaneously (S.C.) or intracerebrally (I.C.V.). *Animals in levodopa experiment received two doses of levodopa or vehicle, the first being given six hours after the last dose of ethanol, the second one hour before observation. The values indicated are computed from the doses of levodopa given on each occasion. The dose of each drug to discoordinate 50% of the animals (FD 50) was compared with the dose that reduced to 50% the proportion of mice showing head-twitches (ED 50).
**Less than ten percent discoordination occurred at top dose tested.
N.T., Not Tested; N.A., Not Applicable.

EXAMPLE 2

Compositions comprising levodopa and a peripheral dopa decarboxylase inhibitor are potentially useful in the prevention or suppression of ethanol withdrawal symptoms in individuals abstaining from ethanol after intoxication therewith. Such compositions contain from 1 to 10 parts by weight of levodopa and 1 part by weight of the inhibitor. Examples of such inhibitors include α-methyl-dopa hydrazine, N'-(D,L-seryl)-N''-(3,4,5-trihydroxybenzyl)-hydrazine and pharmacologically acceptable acid addition salts of either compound such as the hydrochloride and maleate salt. A composition comprising 4 parts of levodopa and 1 part of the inhibitor is preferred. Doses of such compositions which are of potential benefit in the prevention or suppression of withdrawal symptoms in the model experiments described in Example 1 range from 6 mg/kg to 33 mg/kg. In the case of the lower limit, 6 mg/kg, the dose represents 3 mg/kg of levodopa and 3 mg/kg of inhibitor (a 1:1 ratio, by weight, respectively). In the case of the upper limit, the dose represents 30 mg/kg of levodopa and 3 mg/kg of the inhibitor (a 10:1 ratio, by weight, respectively). Preferably, a dose of 15 mg/kg should be utilized, which dose represents 12 mg/kg of levodopa and 3 mg/kg of the inhibitor (a 4:1 ratio, by weight, respectively).

What is claimed is:

1. A method of preventing or suppressing ethanol-withdrawal symptoms in an individual physically dependent on ethanol, which method consists of:
    administering to said individual an effective amount of levodopa to prevent or suppress said symptoms.
2. A method as in claim 1 wherein said amount is from 63 mg/kg to 1213 mg/kg.
3. A method as in claim 1, wherein said amount is 231.5 mg/kg.

* * * * *